United States Patent
Tarassenko et al.

(10) Patent No.: US 8,332,017 B2
(45) Date of Patent: Dec. 11, 2012

(54) METHOD OF BIOMEDICAL SIGNAL ANALYSIS INCLUDING IMPROVED AUTOMATIC SEGMENTATION

(75) Inventors: Lionel Tarassenko, Oxford (GB); Alan Patterson, Oxford (GB); Iain Guy Strachan, Oxon (GB)

(73) Assignee: OBS Medical Limited, Abingdon (GB)

( * ) Notice: Subject to any disclaimer, the term of this patent is extended or adjusted under 35 U.S.C. 154(b) by 570 days.

(21) Appl. No.: 12/517,127

(22) PCT Filed: Nov. 30, 2007

(86) PCT No.: PCT/GB2007/004593
§ 371 (c)(1),
(2), (4) Date: Oct. 2, 2009

(87) PCT Pub. No.: WO2008/065412
PCT Pub. Date: Jun. 5, 2008

(65) Prior Publication Data
US 2010/0056939 A1    Mar. 4, 2010

(30) Foreign Application Priority Data
Dec. 1, 2006 (GB) .................................. 0624081.6

(51) Int. Cl.
*A61B 5/04* (2006.01)
(52) U.S. Cl. ..................................................... 600/509
(58) Field of Classification Search .................. 600/509, 600/523; 704/242
See application file for complete search history.

(56) References Cited

U.S. PATENT DOCUMENTS

| | | | |
|---|---|---|---|
| 5,560,369 A | 10/1996 | McClure et al. | |
| 5,782,888 A | 7/1998 | Sun et al. | |
| 7,941,209 B2* | 5/2011 | Hughes et al. | 600/523 |
| 2003/0060724 A1 | 3/2003 | Thiagarajan et al. | |
| 2003/0204146 A1 | 10/2003 | Carlson | |
| 2005/0234357 A1 | 10/2005 | Xue et al. | |
| 2005/0234363 A1 | 10/2005 | Xue | |
| 2007/0273504 A1 | 11/2007 | Tran | |
| 2008/0132799 A1 | 6/2008 | Xue | |

FOREIGN PATENT DOCUMENTS
WO   WO 2005/107587   11/2005

OTHER PUBLICATIONS

International Search Report for PCT/GB2007/004617 mailed Mar. 14, 2008. Written Opinion of the International Searching Authority for PCT/GB2007/004617, mailed Mar. 14, 2008.

(Continued)

*Primary Examiner* — Brian T Gedeon
(74) *Attorney, Agent, or Firm* — Nixon & Vanderhye, P.C.

(57) ABSTRACT

A method of analysing biomedical signals, for example electrocardiograms, by using a Hidden Markov Model for subsections of the signal. In the case of an electrocardiogram two Hidden Markov Models are used to detect respectively the start and end of the QT interval. The relationship between the QT interval and heart rate can be computed and a contemporaneous value for the slope of this relationship can be obtained by calculating the QT/RR relationship for all of the beats in a sliding time window based on the current beat. Portions of electrocardiograms taken on different days can efficiently and accurately be compared by selecting time windows of the ECGs at the same time of day, and looking for similar beats in those time windows.

19 Claims, 8 Drawing Sheets

OTHER PUBLICATIONS

UK Search Report for GB Application No. 0624085.7, dated Apr. 3, 2007.

Graja et al., "Hidden Markov Tree Model Applied to ECG Delineation" IEEE Transactions on Instrumentation and Measurement, vol. 54, No. 6, (Dec. 2005), pp. 2163-2168.

Hughes, N.P. et al., "Automated QT Interval Analysis with Confidence Measures", Computers in Cardiology, 2004, (Sep. 19-22, 2004), pp. 765-768.

Hoffman, G.S. et al., "A Novel Electrocardiogram Segmentation Algorithm Using a Multiple Model Adaptive Estimator", IEEE Conference on Decision Andcontrol, vol. 1 of 4, (Dec. 10, 2002), pp. 2524-2529.

Hughes et al, "Markov Models for Automated ECG Interval Analysis", (2004), vol. 16, Thrun S, Saul L & Scholkopf B (eds), MIT Press.

* cited by examiner

US 8,332,017 B2

METHOD OF BIOMEDICAL SIGNAL ANALYSIS INCLUDING IMPROVED AUTOMATIC SEGMENTATION

This application is the U.S. national phase of International Application No. PCT/GB2007/004593 filed 30 Nov. 2007, which designated the U.S. and claims priority to Great Britain Application No. 0624081.6 filed 1 December 2006, the entire contents of each of which are hereby incorporated by reference,

BACKGROUND AND SUMMARY

The present invention concerns a method for the analysis of a biomedical signal such as electrocardiograms (ECG) or other biomedical signals.

There are a variety of biomedical signals, i.e. signals representative of the state or condition of a human or animal, which are obtained invasively or non-invasively by the use of monitoring instrumentation. Typical examples include electrocardiograms (ECG), electroencephalograms (EEG), beat-to-beat blood pressure, the photoplethysmograph (PPG), impedance plethysmograph, respiration rate or impedance pneumogram, and blood oxygen saturation which all have regularly repeating patterns. These signals are typically examined by experts to determine, for example, the state of health of the human or animal, the effect of some therapy, for example, a drug, on the human or animal and so on. Such expert analysis is, however, time consuming and expensive. Considerable efforts have therefore been made over the past few years to provide automated techniques for analysing biomedical signals. Such signals are often noisy, complex and highly variable in time and from individual to individual. Automated analysis is therefore difficult, and the large amount of data which can be generated by signal recordings from even one individual over an extended period can make it impractical to analyse all of the data even using computers with fast processors.

An example of an automated signal analysis method for segmentation of electrocardiograms is disclosed in WO 2005/107587. That document discloses the use of a trained Hidden Markov Model to segment individual heartbeats in an electrocardiogram (ECG). The ECG (also known by the acronym EKG) is an important non-invasive signal which measures the electrical activity of the heart.

Each individual heartbeat is comprised of a number of distinct cardiological stages, which in turn give rise to a set of distinct features in the ECG waveform. These features represent either depolarization (electrical discharging) or repolarization (electrical recharging) of the muscle cells in particular regions of the heart. FIG. 1 shows a human ECG waveform and the associated features. The standard features of the ECG waveform are the P wave, the QRS complex and the T wave. Additionally a small U wave (following the T wave) is occasionally present.

The cardiac cycle begins with the P wave (the start and end points of which are referred to as $P_{on}$ and $P_{offset}$), which corresponds to the period of atrial depolarization in the heart. This is followed by the QRS complex, which is generally the most recognisable feature of an ECG waveform, and corresponds to the period of ventricular depolarization (which masks the atrial repolarization). The start and end points of the QRS complex are referred to as the $Q_{onset}$ and J points. The T wave follows the QRS complex and corresponds to the period of ventricular repolarization. The end point of the T wave is referred to as $T_{offset}$ and represents the end of the cardiac cycle (presuming the absence of a U wave). By examining the ECG signal in detail it is possible to derive a number of informative measurements from the characteristic ECG waveform. These can then be used to assess cardiac condition and detect changes or potential abnormalities present in the cardiac rhythm.

A particularly important measurement is the "QT interval", which is defined as the time from the start of the QRS complex to the end of the T wave, i.e. $T_{offset}-Q_{onset}$. This timing interval corresponds to the total duration of the electrical activity (both depolarization and repolarization) in the ventricles.

The QT interval is particularly significant since it is a good indicator of certain medical conditions, and it also has to be monitored in volunteers testing new pharmacological substances in clinical trials. In the past such volunteers would have their ECGs monitored and recorded for relatively short times (for example 10 seconds or so) at regular intervals during a clinical trial. For example in connection with the administration of an experimental drug, 10 second ECG recordings might be made on administration of the drug (time point zero), at 30 minutes, one hour, 1.5 hours and so on up to one day later, but typically decreasing in frequency after the first six hours. Typically, as a control, ECG recordings would also be made at the corresponding times on a day when the volunteer is not administered with the drug, and on a day when the volunteer is administered with a placebo. The effect of the drug on the volunteer's heart, for example whether it lengthens the QT interval, and by how much, will be appraised by experts reviewing the short ECG recordings.

More recently, though, concerns that recording short periods of ECG at spaced intervals through the day might miss certain effects has led to continuous recording of all twelve channels (a so-called Holter recording). This hugely increases the amount of ECG data. While manual analysis is possible with short duration recordings at regularly spaced intervals as above, with a continuous Holter recording, analysis of the 24 hours would require of the order of 100,000 beats (60 bpm×60 minutes×24 hours=86,400) to be analysed per channel. This makes existing methods of expert analysis, and indeed many methods of automated analysis, impractical.

An additional problem which occurs in analysis of ECGs is that the QT interval varies with heart rate. So decreased heart rate leads to increased QT interval. The increase and decrease in QT interval associated with heart rate changes is much greater than the change caused by a pharmacological substance. The heart rate also varies periodically with the breathing cycle, and this periodic change also affects the QT interval. Thus values from the QT interval measured from an ECG are usually corrected by dividing the measured QT interval by the cube root or square root of the beat to beat interval (period from one R peak to the next) in seconds. This correction is not, however, particularly accurate.

Further, in order to reduce the effects of heart rate variation it is normal, when assessing ECGs taken on different days, to compare ECGs taken from the same time on each day. Again, though, this is not particularly accurate.

A first aspect of the present invention provides a computer-implemented method for the analysis of a biomedical signal having multiple identifiable time-sequential segments and at least one recognisable periodic signal feature, the method comprising the step of segmenting the signal using a Hidden Markov Model, the model comprising a plurality of states corresponding to successive segments of the signal; characterised in that:

the segmentation is performed using only two or more states corresponding to a subset of said multiple identifiable time-sequential segments, the subset forming a part of said signal between a start and an end point, in that the position of at least one of said start and end points is estimated by reference to said periodic signal feature, and in that the segmentation is performed only on said part of said signal whose location is based on said estimated position.

Thus the time-sequential states correspond to states of the Hidden Markov Model. The periodic signal feature is one which is recognisable by a standard procedure.

Thus with this aspect of the invention it is possible to perform segmentation of only part of the biomedical signal using a Hidden Markov Model which includes only two or more states corresponding to that part. This makes the segmentation process much less demanding on the processor and thus quicker.

As indicated in WO 2005/107587, the use of the Hidden Markov Model returns a value for the probability of the segmented waveform being drawn from the distribution of waveforms in the training set, and this can be used as a confidence measure.

The present invention however can provide a further confidence measure based on the difference between predicted value of the location of the required feature of the signal being segmented, and the location detected by use of the Hidden Markov Model segmentation.

The invention may be applied to an electrocardiogram and the part of the signal to be segmented can be any one of the standard cardiological stages of the heart beat, for example the QT interval from $Q_{onset}$ to $T_{offset}$. In this case the segmentation can be performed based on an estimated position of $T_{offset}$ whose position can be estimated initially by detection of a salient feature in the waveform such as the R peak or J point (which is easy to detect and identify once the position of the R peak is known), followed by the use of a relationship between the heart rate and QT interval. This relationship may be the standard relationship or can be estimated by analysis of the electrocardiogram signal itself over a period preceding the beat being segmented.

Preferably for analysis the biomedical signal is divided into successive sections, for example 30 second sections in the case of an ECG, with end portions which temporally overlap (by, for example, 10 seconds in the case of an ECG) with the neighbouring sections. This allows the central portion of each section to be taken after segmentation without having a problem of transient or edge effects at the ends of sections.

A second aspect of the invention provides an enhancement to an existing method of correcting variations in the QT interval in an electrocardiogram (ECG) caused by variations in heart rate, the QT interval being the period from $Q_{onset}$ to $T_{offset}$ in the electrocardiogram (ECG), the method comprising finding the values of QT interval and corresponding beat to beat time for each of a plurality of beats in a time period spanning the current beat, the beat to beat time being the time period between the R peak of each beat and the R peak of the previous or next beat, performing regression analysis on the QT intervals and corresponding beat to beat times over said time period to calculate the relationship between the QT interval and beat to beat time, using that relationship to correct the QT interval for the current beat, and performing the regression analysis repeatedly based on a new time period spanning the current beat at that time. Thus the relationship between the RR interval and QT interval is constantly adapted for each beat based on a time window spanning that beat. This thus provides an adaptive contemporaneous individual correction of the QT interval. Preferably the time period is in the region of 4 to 6 hours, this being achieved by looking at the ECG for 2 to 3 hours before and after the current beat and performing the QT-RR regression analysis over each successive 4 to 6 hour period, moving forwards in time one or more beats at a time.

A third aspect of the invention utilises the QT-RR relationship mentioned above as an analysis technique in itself. Thus this aspect of the invention provides a method of analysing an electrocardiogram (ecg), comprising finding, for each of a plurality of beats in the electrocardiogram the current value of the slope of the relationship between the QT interval and R-R interval, the QT interval being the period from $Q_{onset}$ to $T_{offset}$ in a beat in the electrocardiogram (ecg) and the R-R interval being the time period between the R peak of the corresponding beat and the R peak of a neighbouring beat, each current value of the slope being obtained by performing regression analysis on the values of QT intervals and corresponding R-R intervals for beats in a respective time period spanning each of said plurality of beats, the method further comprising displaying the calculated current slope values for each of said plurality of beats, thereby to display variations in said slope through the duration of the Holter recording.

It is found, for example, that the slope of the QT-RR relationship can vary depending on the state of the individual. Certain pharmacological substances, for example, can cause the slope to vary and thus this aspect of the invention provides a way of detecting and monitoring changes in cardiac activity.

Preferably, as before, the respective time periods are of 4 to 6 hours in duration, although different time periods can be adopted in different applications.

Another aspect of the invention provides a method of analysing two biomedical signals of a patient taken on different days, comprising selecting a portion of each of said biomedical signals obtained during the same time period on each of said different days, defining a similarity metric to measure the similarity of subsections of the two portions, using the similarity metric to select a subsection of each of the two portions which are similar, and performing comparative analysis on said selected subsections.

Thus with this aspect of the invention the subsections selected will not necessarily be from exactly corresponding times of day. Instead time windows are defined at the same time of day for the two ECGs and within those time windows subsections which are similar to each other are selected for further comparative analysis.

The similarity metric may measure similarity on the basis of one or more features of the signal, while the comparative analysis is to determine differences in a different feature of the signal. Preferably the subsections are those that have the maximum similarity within the time window.

In the case of an ECG the comparative analysis may be comparing the QT intervals, while the similarity metric measures the heart rate or shape of the waveform. Thus, in the case of an ECG the QT intervals are compared for heart beats which are similar in shape or for heart beats deriving from a portion of the ECG where the heart rate is the same (or as similar a possible).

In the case of an ECG the subsection selected from each of the two portions can be several of the most similar individual beats, e.g. three pairs of beats, or alternatively the comparative analysis can proceed on the basis of an average (e.g. mean or median) value of a feature over the selected subsections.

The present invention can be implemented in the form of a computer program for processing digitised biomedical signals, and the invention extends to such a program, to a storage medium storing such a program and to a computer system programmed to carry out the method.

BRIEF DESCRIPTION OF THE DRAWINGS

The invention will be further described by way of example with reference to the accompanying drawings, in which.

DETAILED DESCRIPTION OF EXAMPLE EMBODIMENTS

An embodiment of the invention will now be described which applies the various aspects mentioned above to the analysis of 24 hour Holter recording of 12 channel electrocardiograms (ECGs).

Figure 1:
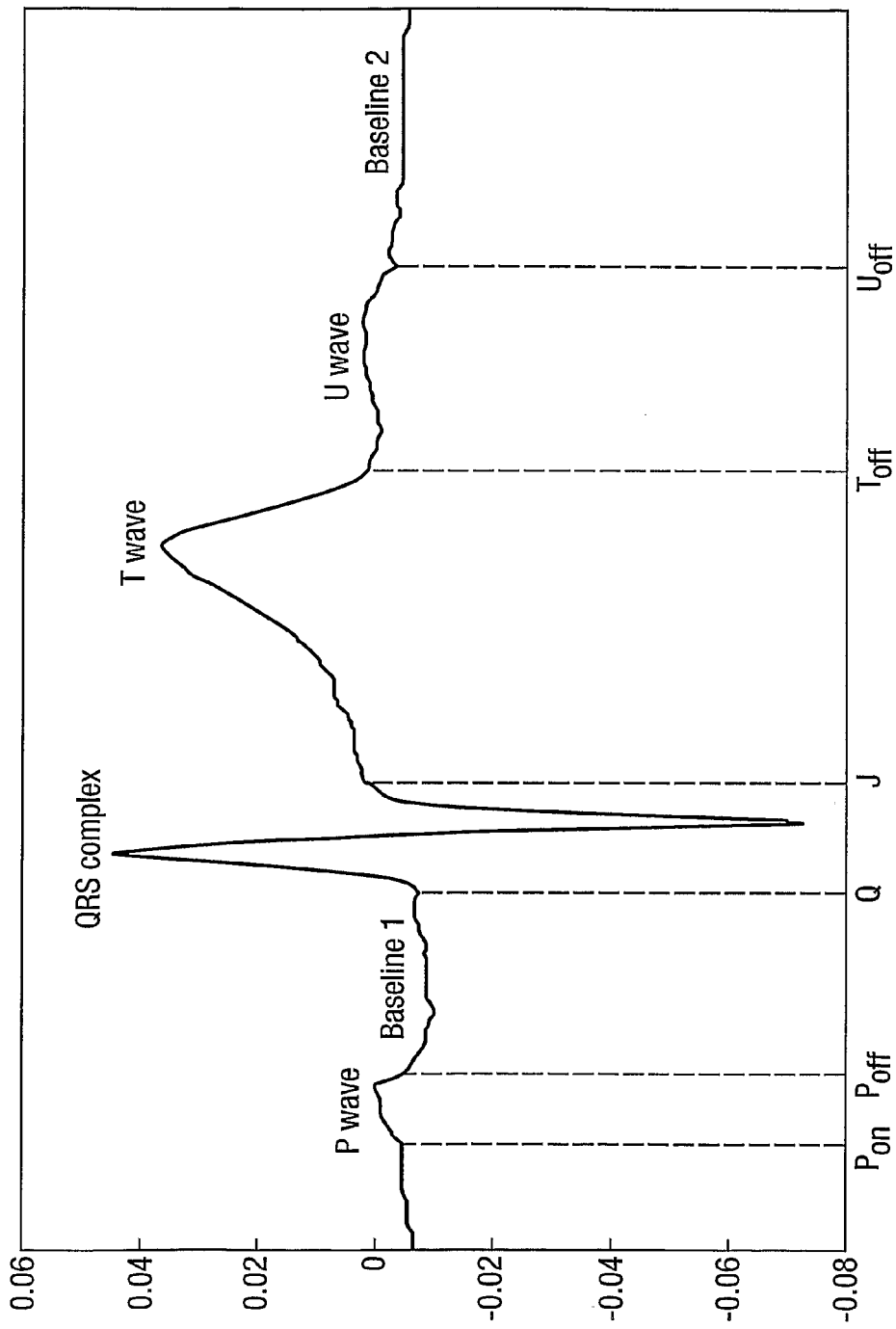
FIG. 1 is an illustration of a single heart beat waveform in an electrocardiogram.

In the following example the segmentation of the ECG relies on the use of a Hidden Markov Model. The published patent application WO 2005/107587, and the papers Hughes NP and Tarassenko L. (2004). *Automated QT Interval Analysis with Confidence Measures. Computers in Cardiology*, pp. 31-34 and Hughes NP, Tarassenko L & Roberts S. (2004). *Markov Models for Automated ECG Interval Analysis. Advances in Neural Information Processing Systems*, vol. 16, Thrun S, Saul L & Scholkopf B (eds), MIT Press., which are incorporated herein by reference, describe how to apply a Hidden Markov Model for the entire extent of the human heart beat waveform as illustrated in FIG. 1. That technique detects the various time points in FIG. 1 corresponding to transitions between different states, in particular $P_{onset}$, $Q_{onset}$, J, and $T_{offset}$ points. It does this by processing the entire ECG waveform and having separate state models for the PR interval, the QRS interval, the T wave and the baseline region between the $T_{onset}$ point and the next P wave onset.

With this embodiment of the present invention the aim is only to detect $Q_{onset}$ and $T_{offset}$ points so that the QT interval can be obtained. This is achieved by using two separate Hidden Markov Models, one of which detects the $Q_{onset}$ point and one the $T_{offset}$, the two models being independent.

The model to detect the $Q_{onset}$ point has states corresponding to a portion of the waveform (typically 50 ms) prior to the $Q_{onset}$ point, and a similar portion of the waveform after the $Q_{onset}$ point (comprising part of the QRS complex), while the model for detecting the $T_{offset}$ point has states corresponding to a portion of the waveform (typically 60 ms) prior to the end of the T wave, and a similar portion of the waveform after the end of the T wave. The models are trained using a training set of manually annotated ECGs in a corresponding way to the full model described in WO 2005/107857, and the papers mentioned above.

Briefly, Hidden Markov Models comprise:

A Transition Model giving the initial probabilities of the hidden states, and a matrix of probabilities giving the probability of transition from one specific state to another specific state at the next observation in time. "Self-transitions" are when the state does not change between measurements.

A set of Observation Models, one for each of the states, each of which gives the probability of being in the said state, given the observations at any given time point.

In this embodiment, the "transition model" is easily derived from a set of manually annotated training data, which defines exactly which state (e.g. P wave, QRS complex, T wave) the model is in, as each state is defined by the time segment between the annotation points placed there by a clinician. Thus for each such segment, and on each manually annotated beat, we may count the number of self-transitions as being the overall number of time samples in that segment, and we also count the single transition from that state to the next one, given by the annotation point. This process is repeated for each state, and for each annotated beat, to give an overall count of samples in each state (from which the initial state probabilities are derived), and also the table counts of each type of transition (from which the transition probabilities may be derived).

The "observation models" may be based on Multivariate Gaussian Mixtures Models (see Bishop C. M. (1995) *Neural Networks for Pattern Recognition* (Chapter 2). OUP, Oxford, 1995 ISBN 0 19 853864) using a full covariance matrix, or an artificial neural network, such as the Multilayer Perceptron, that is trained to output posterior class probabilities, using the "softmax" output function (see Bishop C. M. (1995) *Neural Networks for Pattern Recognition* (pages 238-240). OUP, Oxford, 1995 ISBN 0 19 853864). The observation vectors consist of undecimated wavelet transform (UWT) coefficients and their derivatives (see Percival, D. B., and Walden, A. T., (2000)*Wavelet Methods for Time Series Analysis*. Cambridge University Press.). Training data for each of the state models is again extracted from the training set, with the corresponding state for a sample at a given time defined by the annotation points before and after that time. The Multivariate Gaussian Mixture models may be trained by the standard EM (Expectation-Maximization) algorithm (see Dempster, A. P., Laird, N., and Rubin, D (1977)*Maximum Likelihood from incomplete data via the EM algorithm. Journal of the Royal Statistical Society, B,* 39:-38), If a Multilayer Perceptron is to be used for the observation models, then these may also be trained by a non-linear optimization procedure, such as Scaled Conjugate Gradients. Example implementations of both the EM algorithm and the Scaled Conjugate Gradients non-linear optimization procedure are given in *Nabney, I.T.* (2002) *NETLAB—Algorithms for Pattern Recognition* (3) Springer, London ISBN 1-85233-440-1.

The trained Hidden Markov Model is applied to the input waveforms to segment them in the same way as the full model is applied in WO 2005/107587, except that each of the two models is only applied to a part of the ECG signal as explained in more detail below. For example, this may use the Viterbi Algorithm to find the most probable state sequence (i) and the probability of the sequence, the logarithm of which is used to derive the confidence.

The key features of the segmentation in this embodiment are:

1) The identifiable periodic feature is the R-peak of the waveform, which is detected by a standard algorithm (Pan-Tompkins). (Note that in alternative embodiments any other identifiable feature could be used, such as the J point.)

2) One HMM is used to detect the $Q_{onset}$ point.

3) The known roughly linear relationship between RR and QT is then used to make an initial estimate of the position of the $T_{offset}$ point, which forms the mid-point between the start and end points for the second HMM that locates the $T_{offset}$ point.

4) Furthermore, this estimate is refined by considering each QT interval as part of a time series, rather than independently, so that the next QT interval is predicted based on the value of the current or past QT intervals using a recursive predictive algorithm such as a Kalman filter. Thus the current QT prolongation is tracked, and this gives the current offset with respect to the standard RR/QT relationship.

5) Finally, using the start and end points thereby obtained, the $T_{offset}$ point is then estimated by the second (two-state) HMM, with the two states corresponding to the segment of the waveform just before the $T_{offset}$ point and just after. The transition from the first to the second state marks the determined $T_{offset}$ point.

Figure 2:
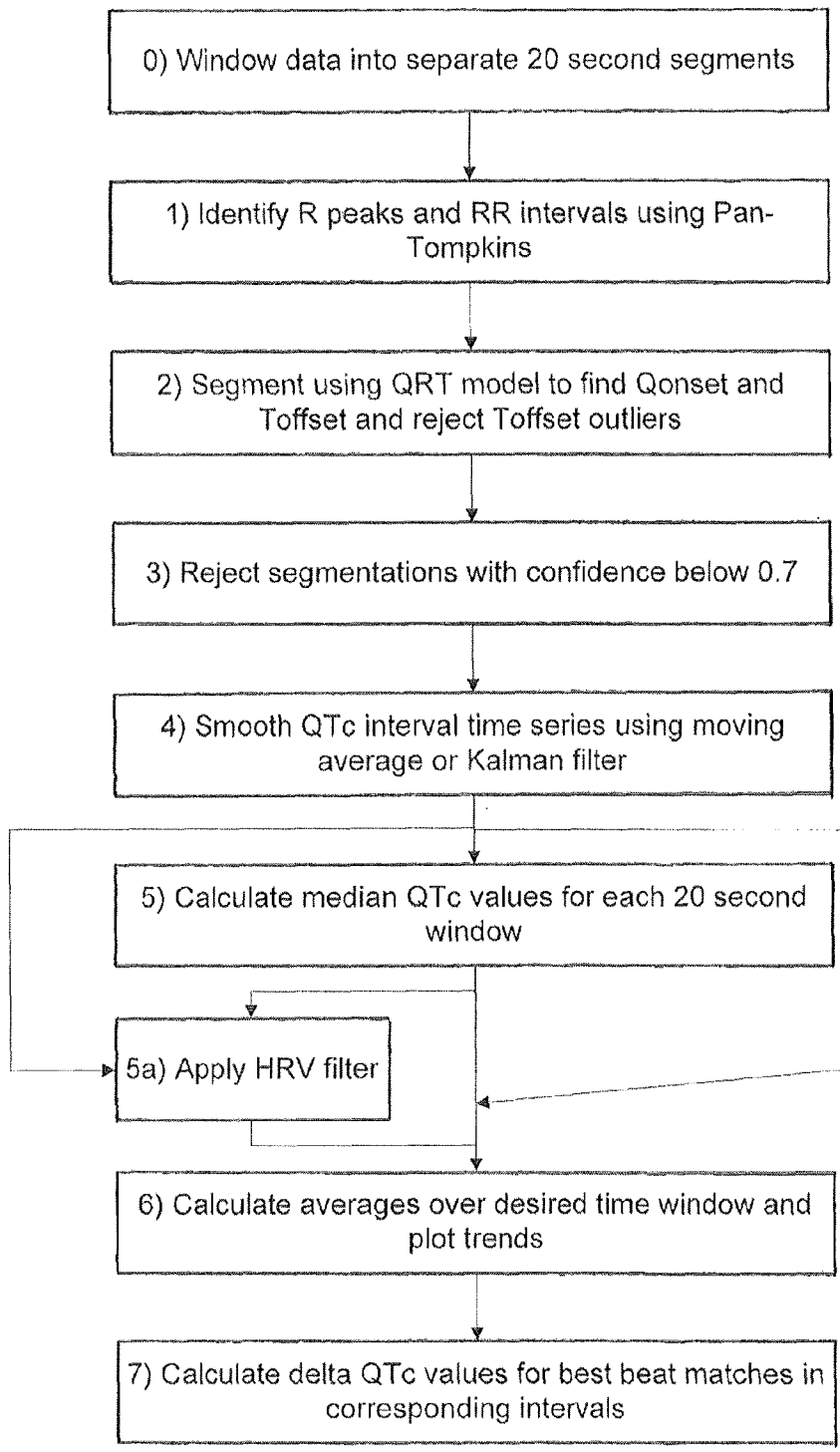
FIG. 2 is a flowchart showing the analysis of electrocardiograms in accordance with one embodiment of the invention.
Figure 3:
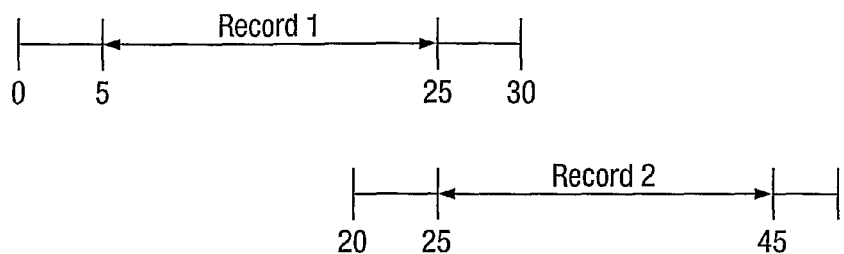
FIG. 3 illustrates how sections of the ECG are windowed for analysis in one embodiment of the invention.

FIG. 2 illustrates the overall flow of this embodiment of the invention. Firstly, in step 0 the input data consisting of digitised ECGs is windowed into separate segments or "records". To produce each record a 30 second segment of ECG data is read from the ECG data file. The segments, however, overlap by 10 seconds at each end as illustrated in FIG. 3. This technique eliminates "edge effects" in the signal processing because only the central 20 second segments, relatively far from the ends, will be taken. Thus, as illustrated in FIG. 3, the second record consists of data starting 20 seconds after the first record. The result is a continuous stream of 20 second segments. The first 5 seconds of data in the Holter recording are not analysed.

In step 1 the R peaks in the waveform are identified using the standard Pan-Tomkins algorithm (see J. Pan and W. J Tompkins, *A Real-Time QRS detection algorithm, IEEE Trans. Biomed. Eng.* BME-32(3) 230-236, 1985). The RR intervals are also measured, in this example by taking the median RR interval over a running window of nine RR measurements. At this stage heart beats can be treated as invalid if their RR measurement differs from the median filtered value by more then 20% (this can occur as a result of ectopic beats or other artefacts).

Figure 9:
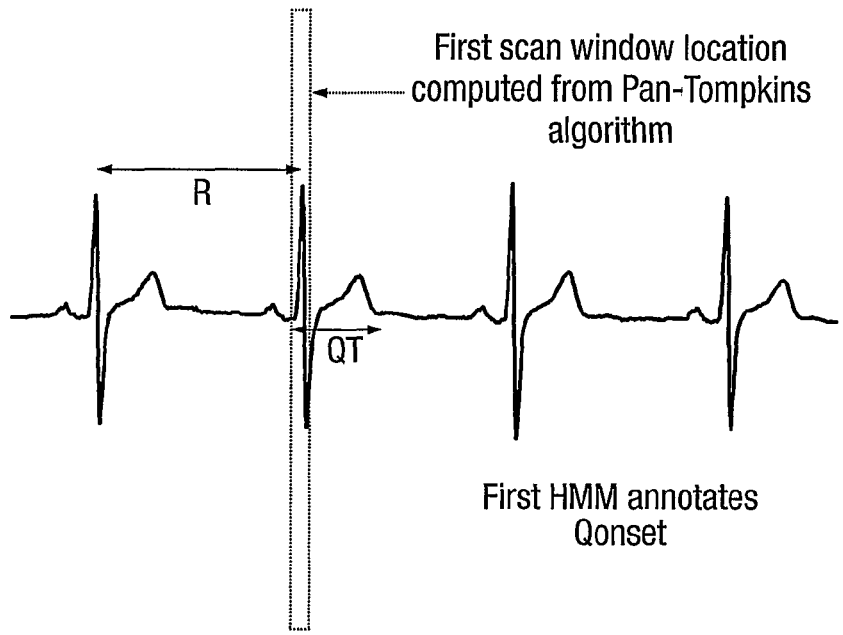
FIG. 9 schematically illustrates the location of the scan window for the first HMM.

In step 2 the two Hidden Markov Models are applied to detect the $Q_{onset}$ and $T_{offset}$ points. To detect $Q_{onset}$ a small sub-segment of the ECG before the detected R wave, shown shaded in FIG. 9, is scanned by the first Hidden Markov Model. The length of the segment scanned is typically 60 ms.

Figure 10:
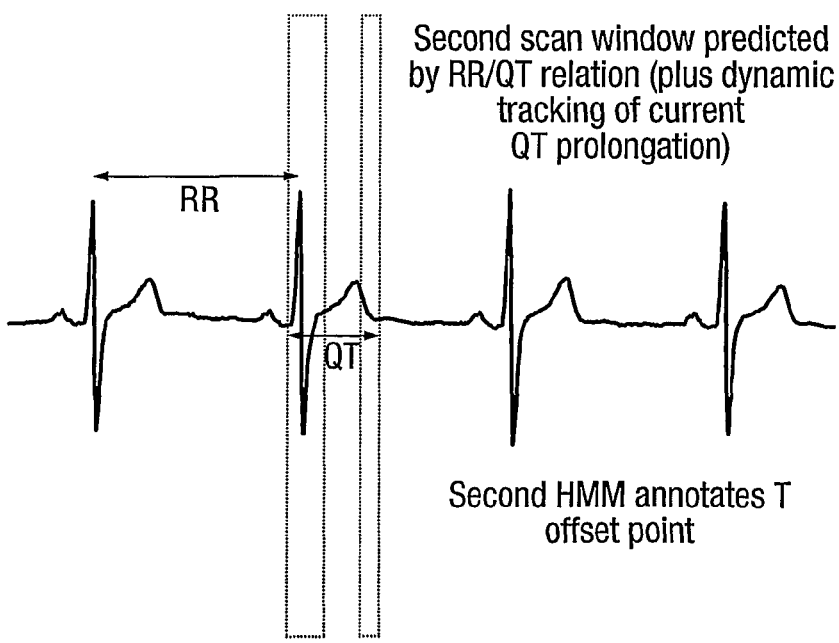
FIG. 10 schematically illustrates the location of the scan window for the second HMM.

To detect the $T_{offset}$ point the value of the preceding RR interval is used to estimate the location of the $T_{offset}$ point. This is done by using a relationship between the RR interval and QT interval derived from a manually annotated training set of ECG waveforms. The RR/QT relationship allows a mean and standard deviation for the QT interval to be estimated given the previous RR interval. Using this estimated $T_{offset}$ point, a sub-segment of the ECG is scanned for three standard deviations either side of the estimated $T_{offset}$ point. This second scan window is shown shaded, together with the first scan window, in FIG. 10.

The RR/QT relationship in this example was only derived from patients that were not given drugs, and hence there was no drug effect causing artificial prolongation of the QT interval. Thus in this embodiment a Kalman filter is employed that tracks the current QT shift relative to the expected (mean) value of the position of the $T_{offset}$ point. This predicted shift is added to the initial estimate obtained by the RR/QT relationship mentioned above.

The two models thus provide the detected $Q_{onset}$ and $T_{offset}$ points and from these the QT interval is calculated.

As mentioned above application of the Hidden Markov Models to segmentation returns a value of the confidence of the segmentation. In step 3 segmentations with a confidence value below 0.7 are rejected.

A second estimate of confidence can be obtained by comparing the located $T_{offset}$ point with the estimated position derived from the QT-RR relationship (and the Kalman Filter based tracking of current QT prolongation). Any waveform for which the difference is greater then two standard deviations is rejected as an outlier.

The above steps provide a time-series of QT interval measurements. These measurements tend inevitably to be noisy, partly due to the variability of the manual measurements used to train the models, also to artefacts and noise present in the signals, as well as occasional errors made by the model. The QT measurement represents a quantity that is expected to change relatively slowly over time, and this can be used to filter out some of the noise in the measurements.

Step 4 indicates two alternative ways of filtering the QT interval measurements, namely by a moving average or by Kalman filtering. The moving average filtering can be, for example, by a simple ten point moving average where each QT interval measurement is taken to be the average of a ten beat window of beats. Recalling that sometimes beats are rejected by steps mentioned above, where a beat is missing the QT value for that beat can simply be taken to be the same as for the previous beat. As an alternative for moving average filtering, a Kalman filter can be used which, as is well known, maintains a predicted value for the QT interval, this predicted value being constantly corrected by a small factor proportional to the difference between the current predicted value and the current measured value. It therefore provides a smooth QT interval estimate.

The QT intervals are also corrected for an effective heart rate of 60 bpm. There are several known formulae that can be used for this correction, such as Bazett's formula (for which the corrected values are designated as QTcB), Fridericia's formula (for which the corrected values are designated as QTcF), and the Individual Contemporaneous correction formula (giving QTcIc), or the adaptive QTcIc mentioned below. The QT intervals corrected by whichever method will be designated as QTc in the following.

The smoothed QTc values from step 4 may be passed directly to step 6 for averages and trends to be plotted on a beat-by-beat basis. Thus because of the speed of the algorithm and automatic rejection of low confidence beats, automated beat-by-beat analysis of continuous 24 hour recordings is possible.

Alternatively, median QTc values may be calculated and plotted as described below.

Where median values are required, in step 5 for each 20 second window of data the median QTc interval is taken This is chosen by ranking the QTc intervals that have not been rejected from the previous steps and choosing the middle value in the series if there is an odd number of beats or the average of the two middle values if there is an even number of beats. If the number of valid QTc intervals is lower than three then the median QTc value is not calculated and the main window is marked as producing invalid data.

It is well known that the QT interval changes with the heart rate. However, when the heart rate changes sufficiently quickly there is a period of adjustment before the QT length stabilises to match the new heart rate. Optionally the method of FIG. 2 can include step 5a which filters out measurements made during periods of heart rate adjustment. Such a heart rate variability (HRV) filter can operate by computing a heart rate variability index over a one minute period. There are many known measures of HRV, both in the time domain and the frequency domain. One measure of heart rate variability may be the standard deviation of the heart rate divided by the mean heart rate over all the beats in the given minute. If this value exceeds a threshold, typically 0.1, then all the beats for that minute and the following minute are discarded. This can apply to the QTc values of step 4 or the median values of step 5.

In step 6 the smoothed median data from step 5 or the filtered data from step 5a are used to calculate average QTc intervals. These averages may be taken over processing windows, e.g. of 30 seconds in length, which are advantageously slid along over the data one (or a few) beat at a time, to give an average QTc interval for each beat in the entire (e.g. 100,000 beat record). These averages can be tabulated and plotted for graphical display.

In step 7 delta QTc values (i.e. the difference in QTc values with drug or placebo and from one day to another) are calculated, together with the mean and standard deviation of the delta QTc values over the time window under consideration (e.g. 30 seconds), these being the required measurements in a clinical trials protocol.

Figure 4:
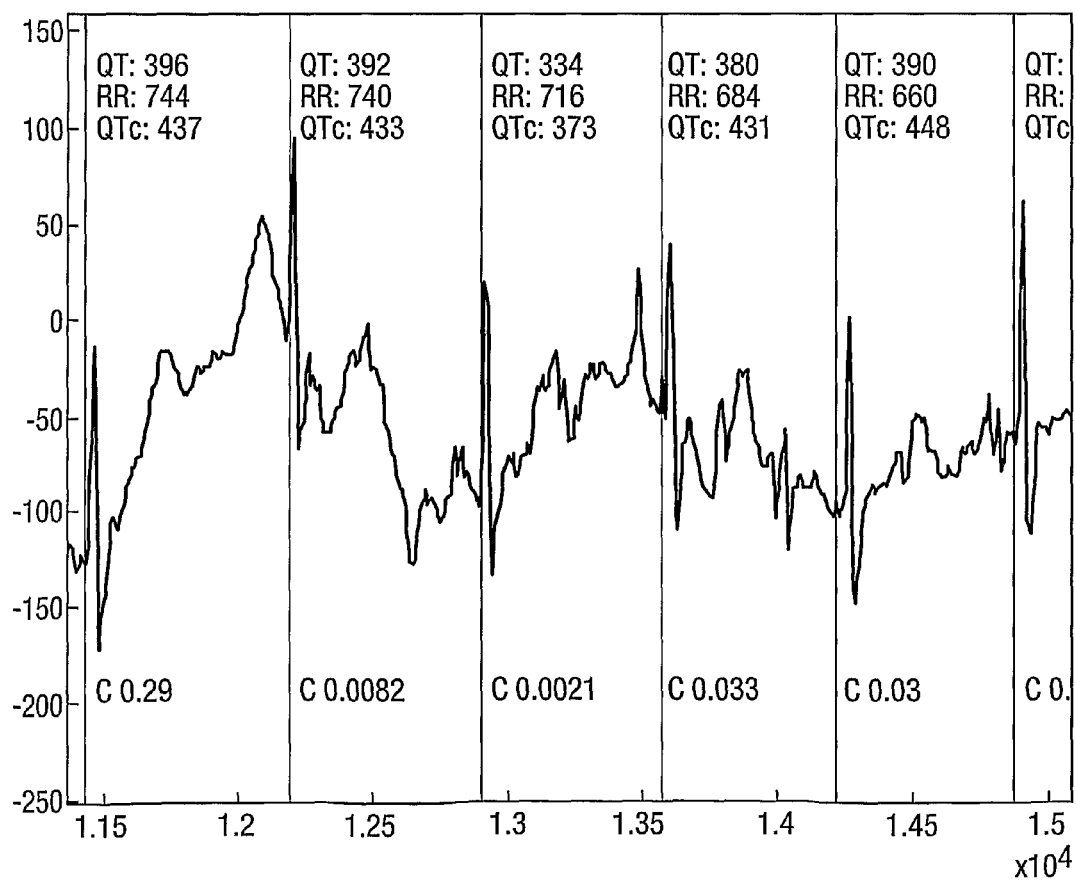
FIG. 4 illustrates the results of segmenting a noisy ECG signal using an embodiment of the invention.
Figure 5A:
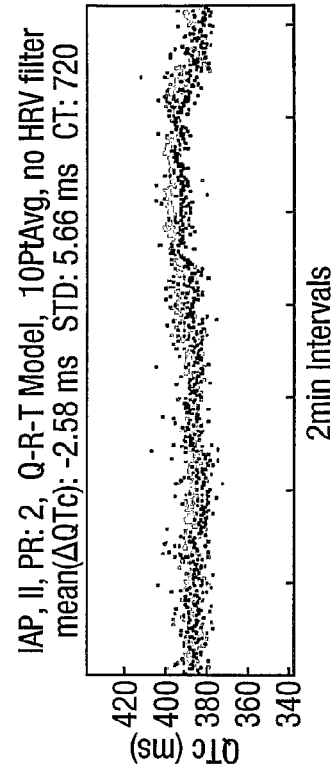
FIG. 5(*a*) to (*h*) illustrate QT and heart rate plots obtained using an embodiment of the invention for a volunteer undergoing two different protocols of a clinical trial.
Figure 5B:
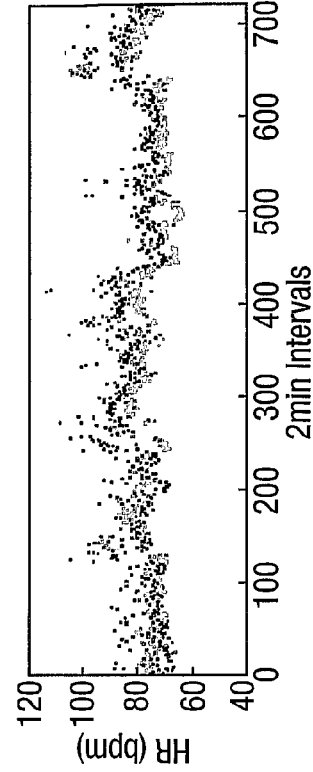
Figure 5C:
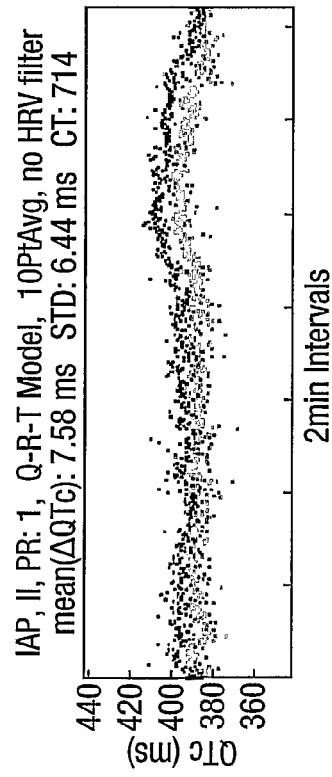
Figure 5D:
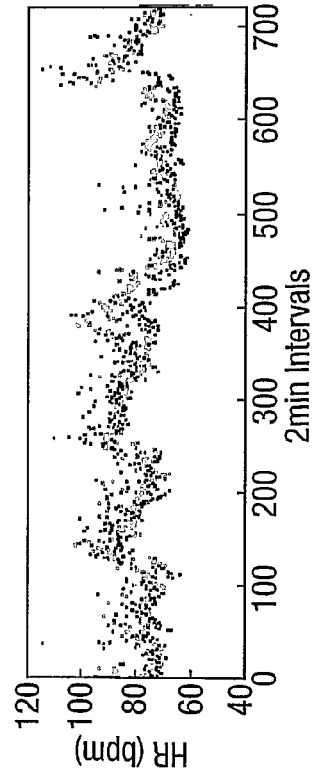
Figure 5E:
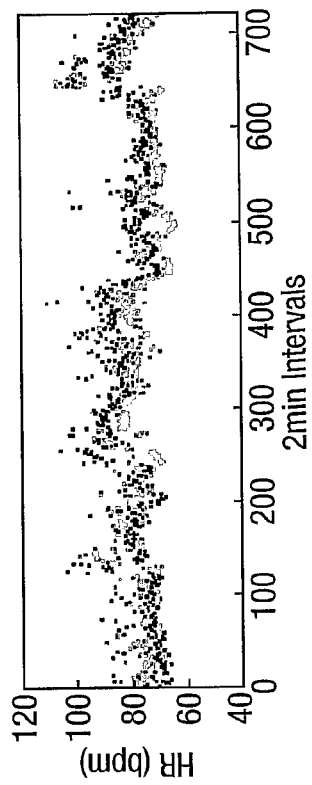
Figure 5F:
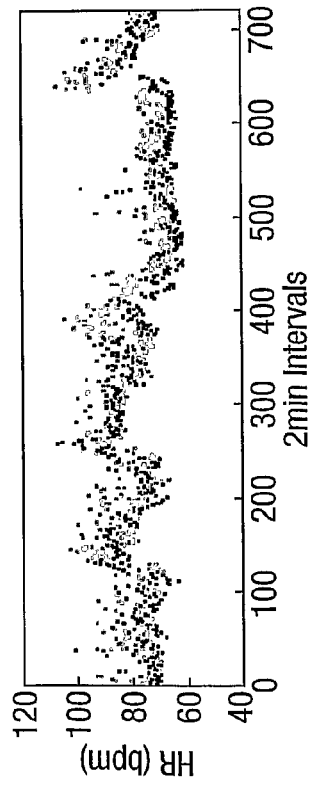
Figure 5G:
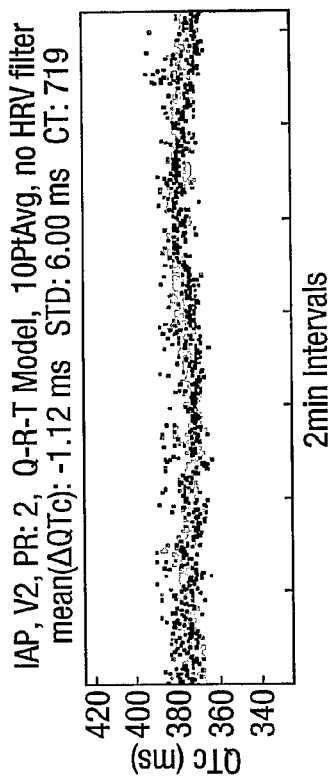
Figure 5H:
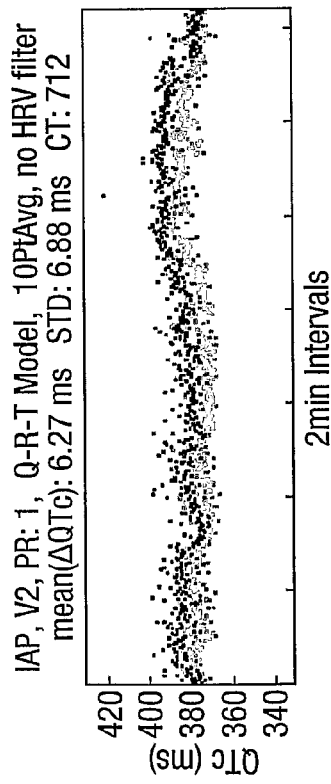

FIG. 4 illustrates an example of the detection of the QT interval on a noisy ECG signal. Despite the high noise content and base line shifts in the ECG, the Q onset locations occur at regular intervals indicating that the correct locations have been found. This is an advantage of the present invention because beats can be correctly identified on the basis of the R peak which can be robustly detected, and the Hidden Markov Models are only applied to limited subsections of the ECG meaning that they are unaffected by noise outside those sections. This allows the present invention to segment heart beats with greater confidence than other techniques.

FIG. 5 illustrates a graphical example of QT interval lengthening for a volunteer in a clinical trial of a pharmacological substance. FIGS. 5a and b illustrate respectively the corrected QT interval and heart rate values for each two minute intervals of lead II for a volunteer on protocol one of a clinical trial of a drug. Values for baseline day (no drug or placebo) are plotted in blue and drug or placebo day are plotted in red. FIGS. 5c and d show corresponding values for the same patient on protocol 2 of the clinical trial. FIGS. 5e and f show protocol 1 results from lead V2 of the ECG of the same patient and FIGS. 5g and h values for ECG lead V2 for protocol 2. It can be seen that for protocol 1 on both leads the red, corrected QT interval values for drug or placebo day are systematically greater than the corrected QT interval values for baseline day. This effect is not visible in protocol 2. The results for protocol 1 give mean delta QTc values of 7.58 ms and 6.27 ms for leads 11 and V2 respectively. The results for protocol 2 show mean delta QTc values of −2.58 ms and 1.12 ms for leads 11 and V2 respectively. Thus these plots successfully detect the administration of the drug lengthening QT interval on drug/placebo day of protocol 1 in this clinical trial.

Beat Matching

In the specific example above the median corrected QT intervals derived from step S (optionally filtered in step 5a) are used to calculate and plot an average corrected QT interval for each successive two minute section of the data. However, the activities of the subject (patient or volunteer) and indeed the start time of the recordings, varies from day-to-day. To allow for this variability the current practice for comparing ECG data from day-to-day is to look at specific time windows at the same time of day on each of the days being compared. For example ten minute windows of data may be inspected at a defined start time each day and at 30 minutes, 60 minutes, 90 minutes, etc. thereafter. In the case of a clinical trial the start point may be the time of administration of a drug or control, or a set time before administration, and the spacing between the time windows may increase through the day. Because of the variability and noisy nature of the data, however, such comparisons may be inaccurate.

Figure 8:
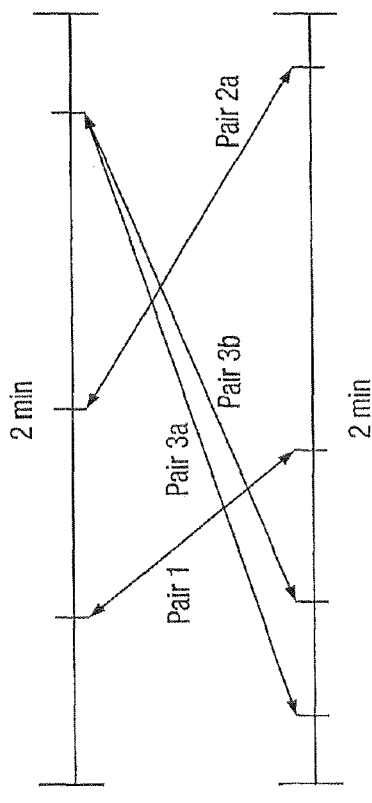
FIG. 8 schematically illustrates looking for matching beats in corresponding time windows on two different days.

To alleviate this problem, in one embodiment of the present invention time windows (e.g. of a few minutes) are defined spanning each standard time point during the day and within these windows pairs of matching beats are found. This is illustrated in FIG. 8. Thus the corrected QT intervals will be compared of two beats which match as closely as possible in some other aspect. The two beats may not occur at precisely the same time of day, but will be within the same time window. Two possible ways of finding the matching beats are:

(1) Consider all the high confidence beats from the corresponding time segment (for example 10 minutes) on each day. Compute some feature that is a measure of similarity for each beat in the two days (for example R-R interval, or some shape indicator). Find the median value of the feature for the combined set of the time segments for the two days. Then, for each of the time segments, rank the beats in terms of their difference from the common median value of the computed feature. For each segment, only select the beats that are closest to the median feature (for example discard the 10 percent of beats that are furthest away). Then compute the mean or median QTc value for each of the beats remaining in each of the time segments, and subtract the two values.

(2) Perform pairwise comparisons for a similarity measure of all beats in one time segment to all beats in the second time segment. For each beat, compute the difference between the QTc value of that beat and the beat (or beats) that match it most closely in the other segment. At the end of this, compute the mean and standard deviation of all the pairwise QTc comparisons thus obtained.

Improved OT/RR Relationship

In the example above it was mentioned that a relationship between RR interval and QT interval derived from the training set of ECGs is used to predict the QT interval.

Figure 6:
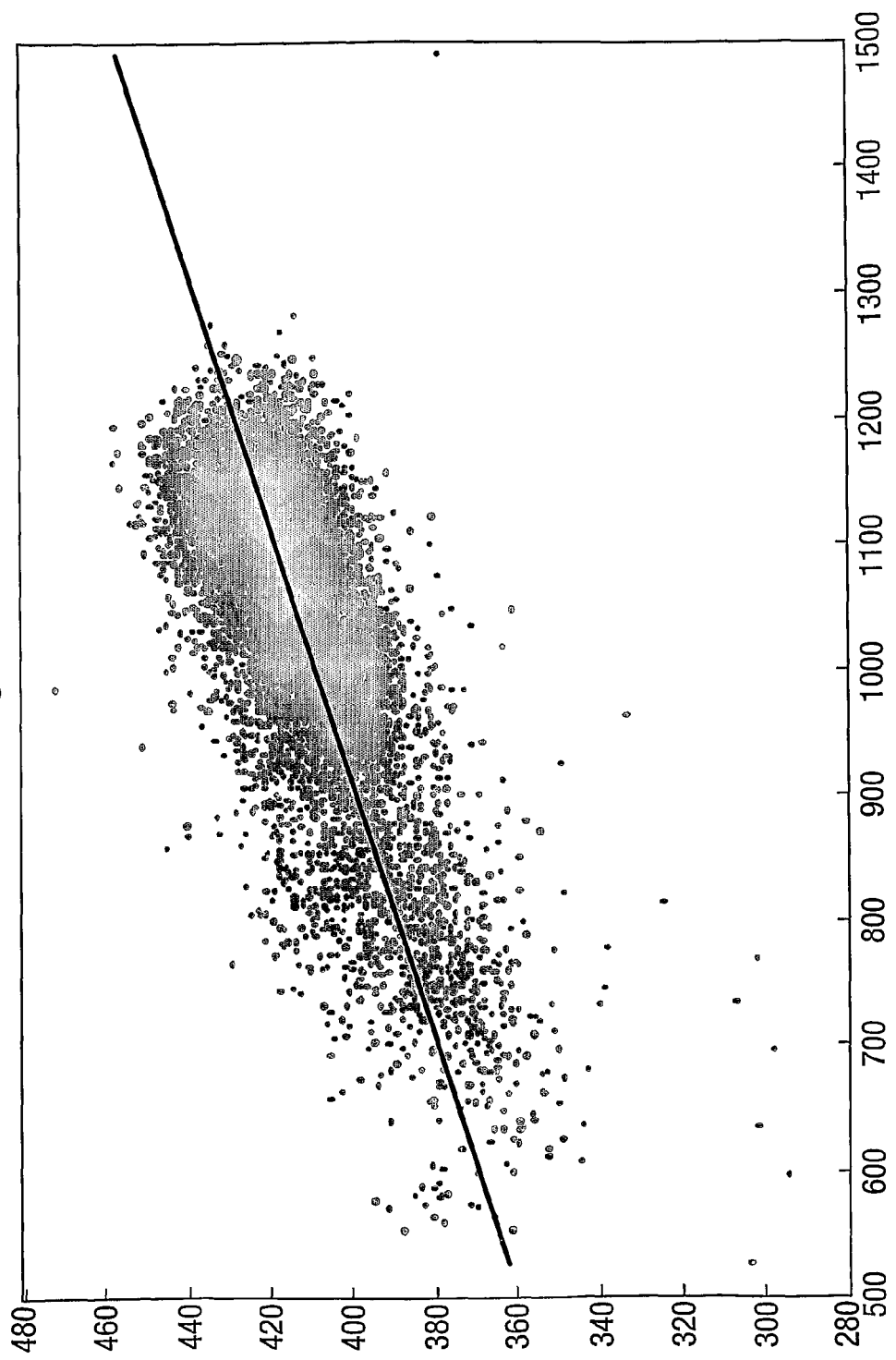
FIG. 6 illustrates an exemplary QT/RR relationship.

One aspect of the present invention, however, utilises a continuously updated QT/RR relationship as a detector of changes in cardiac activity. As an example, for each beat in a set of ECG data the RR interval and QT interval values for all of the beats in a window of two or three hours either side of the current beat are plotted. FIG. 6 graphically illustrates such a plot for the first six hours of a Holter recording and regression analysis is used to compute the slope of the relationship to give the regression line as illustrated in FIG. 6.

This procedure is repeated for each beat in the ECG, thus giving a value of the slope of the relationship for a sliding window, e.g. of plus or minus two, three, four or six hours, based on each beat.

Using this relationship, which is now contemporaneous for each beat, the QT interval obtained from step 2 of FIG. 2 can be corrected using the formula below to provide a corrected Individual contemporaneous estimate of QT, here denoted $QT_{cIc}$. The corrected Individual contemporaneous estimate $QT_{cIc}$ is calculated as follows: —

$$QT_{cIc} = QT + \Delta(QT/RR) \times (1000 - RR)$$

where Δ(QT/RR) is the gradient of the observed QT-RR linear regression over the time period of interest and the QT and RR intervals are expressed in milliseconds.

Figure 7A:
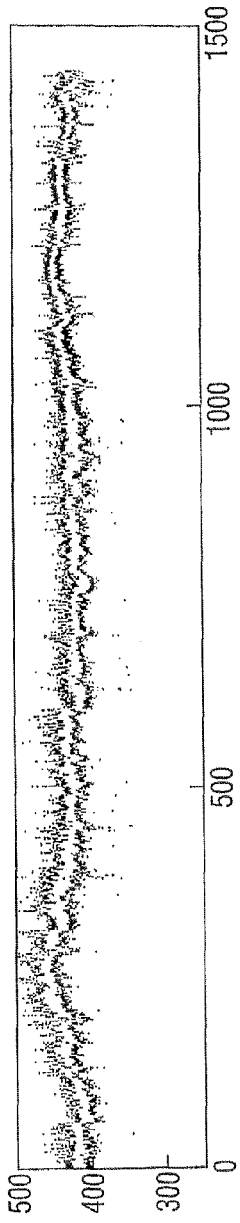
FIGS. 7(*a*) and 7(*b*) illustrate comparative plots of QT interval and QT/RR slope obtained using an embodiment of the present invention for a volunteer receiving a dose of a drug affecting cardiac activity.
Figure 7B:
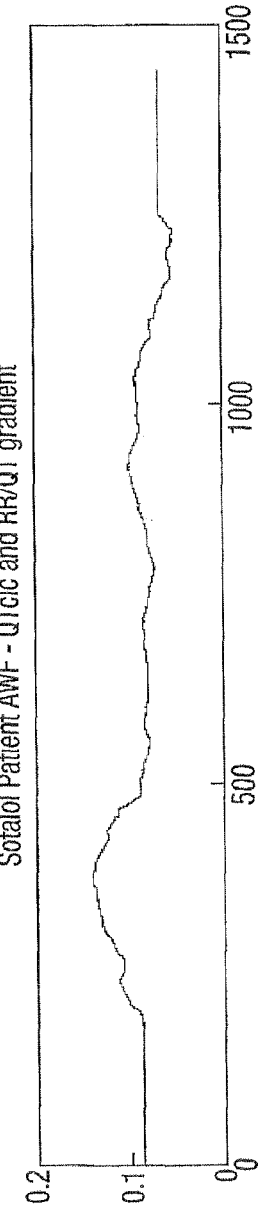

The QT/RR slope is plotted against time for the duration of the ECG data. An example plot is illustrated in FIG. 7(b) aligned with a plot of QT interval (contemporaneously corrected as explained above). FIG. 7(a) illustrates that there is a QT interval prolongation about four hours after administration of the drug in this case, and FIG. 7(b) illustrates that there is a time-delayed increase in QT/RR slope, which reaches its maximum about 5.5 hours after the administration of the drug. Thus monitoring the value of the QT/RR slope on a continual basis can be used as an indicator of variations in cardiac activity.

We claim:

1. A computer-implemented method for analysis of an electrocardiogram, the method comprising segmenting the electrocardiogram into different segments corresponding to different cardiac features using a Hidden Markov Model, the model comprising a plurality of states corresponding to the different cardiac features;
   wherein:
   the segmenting is performed using two or more Hidden Markov Models corresponding only to a subset of the cardiac features the subset comprising the QRS co ex and the T wave within the QT interval of an electrocardiogram, the QT interval being the period from $Q_{onset}$ to $T_{offset}$ in the electrocardiogram,
   the segmenting to identify the T wave bein erformed based on the estimated position of $T_{offset}$ as the end point of the QT interval, and
   wherein the position of the endpoint of the QT interval is obtained from a relationship between heart rate and QT interval.

2. The method according to claim 1, wherein a confidence measure is calculated based on a difference between the position of the start or end point as estimated by reference to the R peak or J point of the electrocardiogram and as obtained from the segmenting.

3. The method according to claim 1, wherein a confidence measure is calculated based on a probability of the segmenting obtained from the HMM.

4. The method according to claim 2, wherein the confidence measure is used to reject automatically artifacts in the electrocardiogram.

5. The method according to claim 1, wherein the relationship between heart rate and QT interval is obtained by analysis of the electrocardiogram over a period preceding the beat being segmented.

6. The method according to claim 1, further comprising correcting variations in the QT interval in the electrocardiogram caused by variations in heart rate, the method further comprising finding values of QT interval and corresponding beat to beat time for each of a plurality of beats in a time period spanning a current beat, the beat to beat time being the time period between the R peak of each beat and the R peak of a neighbouring beat, performing regression analysis on the QT intervals and corresponding beat to beat times over the time period to calculate a relationship between the QT interval and beat to beat time, and using that relationship to correct QT for current beat, wherein the regression analysis is periodically repeated based on a new time period spanning the current beat at that time.

7. The method according to claim 6, wherein the regression analysis is repeated for each beat based on the time period spanning each respective beat.

8. The method according to claim 6, wherein the time period spanning the current beat is the time period from 2 or 3 hours before to 2 or 3 hours after the current beat.

9. The method according to claim 1, further comprising finding, for each of a plurality of beats in the electrocardiogram a current value of the slope of the relationship between the QT interval and R-R interval, the R-R interval being the time period between the R peak of the corresponding beat and the R peak of a neighbouring beat, each current value of the slope being obtained by performing regression analysis on values of QT intervals and corresponding R-R intervals for beats in a respective time period spanning each of the plurality of beats, the method further comprising displaying the calculated current slope values for each of the plurality of beats, thereby to display variations in the slope through the electrocardiogram.

10. The method according to claim 9, wherein the respective time periods are each the time period of from 4 to 6 hours spanning each respective one of the plurality of beats.

11. The method according to claim 1, further comprising analysing two electrocardiograms of a patient taken on different days, comprising selecting a portion of each of the electrocardiograms obtained during the same time period on each of the different days, defining a similarity metric on the basis of one or more features of the electrocardiograms to measure similarity of subsections of the two portions, using the similarity metric to select a subsection of each of the two portions which are similar, and performing comparative analysis on the selected subsections to determine changes in a feature of the electrocardiograms different from the one or more features of the signal.

12. The method according to claim 11, wherein the step of selecting a portion of each of the electrocardiograms obtained during the same time period on each of the different days comprises selecting a time of day and setting as the time period a time window relative to that time point.

13. The method according to claim 11, further comprising selecting a plurality of times of day and setting a time window relative to each of them.

14. The method according to claim 11, wherein the similarity metric measures shape of the waveform of the electrocardiograms.

15. The method according to claim 11, wherein the comparative analysis is QT interval measurement.

16. The method according to claim 11, wherein the similarity metric measures the heart rate.

17. The method according to claim 11, wherein the subsections selected for comparative analysis are several of the most similar individual beats in the portions of the electrocardiograms.

18. The method according to claim 17, wherein three beats are selected.

19. The method according to claim 11, wherein the comparative analysis is on the basis of a value of a feature of the electrocardiograms averaged over each of the two subsections.

* * * * *